(12) United States Patent
Gafni et al.

(10) Patent No.: US 6,741,895 B1
(45) Date of Patent: May 25, 2004

(54) VAGINAL PROBE AND METHOD

(75) Inventors: Ehud Gafni, Ramat-Yishai (IL); Aharon Cohen, Kiriat-Mozkin (IL)

(73) Assignee: Medoc Ltd., Ramat-Yishai (IL)

( * ) Notice: Subject to any disclaimer, the term of this patent is extended or adjusted under 35 U.S.C. 154(b) by 0 days.

(21) Appl. No.: 09/807,753

(22) PCT Filed: Oct. 21, 1999

(86) PCT No.: PCT/IL99/00555

§ 371 (c)(1), (2), (4) Date: Apr. 17, 2001

(87) PCT Pub. No.: WO00/23030

PCT Pub. Date: Apr. 27, 2000

(30) Foreign Application Priority Data

Oct. 22, 1998 (IL) .................................................. 126723

(51) Int. Cl.[7] .................................................. A61N 1/00
(52) U.S. Cl. ......................................... 607/138; 600/38
(58) Field of Search .................... 600/38, 437, 438, 600/442, 443, 446, 451, 454, 456, 457, 459, 462, 463, 472, 481, 500, 504; 128/845; 601/15, 21, 46, 48, 70, 72, 73, 78, 80; 607/96, 113, 115, 118, 138, 145, 146, 148, 150, 153

(56) References Cited

U.S. PATENT DOCUMENTS

| | | |
|---|---|---|
| 3,626,931 A | 12/1971 | Bysakh |
| 3,800,800 A | 4/1974 | Garbe et al. |
| 4,396,019 A * | 8/1983 | Perry, Jr. .................... 600/546 |
| 4,541,439 A * | 9/1985 | Hon ............................ 600/504 |
| 4,616,640 A * | 10/1986 | Kaali et al. .................. 128/830 |
| 4,757,823 A * | 7/1988 | Hofmeister et al. ......... 600/437 |
| 4,869,258 A | 9/1989 | Hetz |
| 4,909,263 A | 3/1990 | Norris |
| 4,911,149 A | 3/1990 | Borodulin et al. |
| 4,972,839 A | 11/1990 | Angelsen |
| 5,007,437 A | 4/1991 | Sterzer |
| 5,046,511 A | 9/1991 | Maurer et al. |
| 5,388,583 A | 2/1995 | Ragauskas et al. |
| 5,499,631 A * | 3/1996 | Weiland ..................... 600/547 |
| 5,562,717 A | 10/1996 | Tippey et al. |
| 5,573,499 A | 11/1996 | McAllister |
| 5,662,699 A | 9/1997 | Hamedi et al. |
| 5,690,604 A | 11/1997 | Barnett |
| 5,699,805 A | 12/1997 | Seward et al. |
| 5,725,473 A | 3/1998 | Taylor |
| 5,782,778 A * | 7/1998 | De Briere et al. .......... 600/587 |
| 5,833,611 A | 11/1998 | Tepper et al. |
| 5,851,175 A | 12/1998 | Nickell |
| 5,875,778 A | 3/1999 | Vroegop |
| 5,881,731 A | 3/1999 | Remes |
| 5,916,173 A | 6/1999 | Kirsner |
| 6,169,914 B1 | 1/2001 | Hovland et al. |

* cited by examiner

Primary Examiner—John P. Lacyk
(74) Attorney, Agent, or Firm—Fenster & Company

(57) ABSTRACT

A vaginal probe, and method of use is disclosed for stimulation of the nerves of the vagina with the purpose of testing their reaction to stimuli in the hope of defining, and treating sexual dysfunction in women. One embodiment of the invention (20) includes a shaft (22) adapted to be inserted into the genetalia of a human female. The shaft (22) includes a stop (24), presented as a thickening of the shaft (22). The probe (20) includes at least one stimulation area (26, 28) defined on a portion of the shaft (22) so that only a selected portion of the genetalia is stimulated. The shaft (22) may have sensors for measuring the reaction of the nerves to stimulation, and the stimulation areas (26, 28) may stimulate the nerves of the vagina using temperature, vibration, electricity, and/or pressure.

116 Claims, 7 Drawing Sheets

VAGINAL PROBE AND METHOD

RELATED APPLICATIONS

This application is a U.S. national filing of PCT Application No. PCT/IL99/00555, filed Oct. 21, 1999, the disclosure of which is incorporated herein by reference.

FIELD OF THE INVENTION

The invention relates in general to the field of peripheral nerve evaluation and in particular to intra-vaginal nerve evaluation.

BACKGROUND OF THE INVENTION

Recent research has shown that one cause of lack of female sexual satisfaction is a paucity of blood flow to the female sex organs. Common types of (organic) female sexual dysfunction include: discomfort during sexual intercourse, dryness, increased time for arousal, diminished ability to reach orgasm and diminished clitoral sensation. A recently marketed pharmaceutical, sold under the name "Viagra", solves a similar problem of impotence in men, by increasing the flow of blood to the male sex organs. As a prelude to permitting this and other drugs for female sexual disorders, the FDA (Food and Drug Administration) requires comprehensive testing into the effects of such drugs. Thus, this and other known therapies for male sexual dysfunction are not currently being applied towards female sexual dysfunction.

In general, the field of study of female sexual dysfunction lags far behind the study of male sexual dysfunction. For example, the following diagnostic tools are currently available for males with erectile dysfunction:

a) Home measurement of nocturnal erection.

b) Vascular tests, such as Doppler, Arteriography and erection causing pharmaceuticals.

c) Neurogenic tests, such as Biothesiometry (vibration stimulation) of the penile shaft, thermal testing of a penis and lower extremities, bulbacavernous reflex measurement and nerve conduction studies.

There exist several methods of measuring blood flow to the female sex organs, including an oxygenation temperature method and a vaginal pulse amplitude method, which utilizes a photoplethysmograph. However, these methods measure the result of sexual arousal (e.g., blood flow) and do not provide an objective measure of the sensitivity of the sex organs.

SUMMARY OF THE INVENTION

An object of some preferred embodiments of the invention is to provide a method and apparatus for measuring a sensitivity of female sex organs, especially of the vagina and/or the clitoris. In a preferred embodiment of the invention, the results of the measurement may be used to diagnose sexual dysfunction, to determine an appropriate pharmaceutical regiment and/or for research into cures for sexual dysfunction.

An aspect of some preferred embodiments of the invention relates to measuring various parameters of nervous sensitivity inside a vagina of a patient and/or at the clitoris of the patient. In a preferred embodiment of the invention, the nervous sensitivity is measured by subjecting a small part of the vagina to a stimulation and accepting feedback, preferably verbal, from the patient. Alternatively or additionally, the stimulation is applied simultaneously to a significant portion of the vagina, for example most of it, for example, by providing stimulation over the entire inserted surface of the probe. Preferably, one or more of the following four thresholds are determined: sensing threshold, pleasure threshold, pain threshold and tolerance threshold. In a preferred embodiment of the invention, physiological parameters may be determined at the part of the vagina, preferably simultaneously with the nervous sensitivity determination. Alternatively or additionally, a physical response of the part of the vagina to the stimulation may be measured, for example an increase in muscular tension or in blood flow. These physiological measurements may be used instead of or in addition to a patient feedback. In a preferred embodiment of the invention, one or more of the following stimuli are used: heat, cold, vibration, ultrasound, pressure and electric current.

An aspect of some preferred embodiments of the invention relates to mapping a response of the vagina and/or selecting a particular part of the vagina to be measured. In a preferred embodiment of the invention, measurements of physiological and/or nervous sensitivity parameters are performed for many parts of the vagina, covering a significant portion thereof. Alternatively or additionally, the measurements may be performed at external sex organs, such as the clitoris or the outer lips of the vagina. Alternatively or additionally to spatial mapping, the measurements may be repeated under various conditions, for example arousal levels, drugs, repetition and/or elapsed time.

An aspect of some preferred embodiment of the invention relates to a vaginal measurement probe which is adapted to match physiological parameters of the measurement task. In a preferred embodiment of the invention, a diameter and/or length of the probe is matched to the vagina and/or to a penile shaft of a regular partner of the patient. Alternatively or additionally, a cross-section of the probe is matched. Alternatively or additionally, an axial geometry variation of the probe, for example a bending in the probe is matched to a penil geometry. Alternatively or additionally, a surface temperature of the probe is controlled, for example matched to a penile surface temperature. Alternatively or additionally, a press profile of the probe, i.e., the level of pressure exerted by the probe against the vaginal structure is matched to a desired profile.

An aspect of some preferred embodiments of the invention relates to a female genital probe including a means, especially a base for maintaining a fixed spatial position of the relative to the female genitalia and/or for applying a desired amount of pressure against a stimulated area Preferably, the probe includes a spring or counter-weight for balancing the probe and/or for affecting a desired level of pressure. Alternatively or additionally, the probe may include a sensor for sensing physiological motion of the patent, such as caused by breathing. Thus, measurements by the probe may be synchronized, windowed and/or corrected for physiological motion.

An aspect of some embodiments of the invention relates to combining stimulation of male or female sex organs with functional imaging to assess the effect of the stimulation. Preferably, female sex organs are stimulated. In a preferred embodiment of the invention, the imaging is of the stimulated organ and/or a stimulated portion thereof. Preferably, blood flow imaging is used. Alternatively or additionally, Heat imaging is used. In a preferred embodiment of the invention, MRI imaging is used. Alternatively or additionally, ultrasonic imaging (from near the stimulated area or outside the body) is used. Alternatively or additionally to using imaging techniques, non-imaging techniques, such as known in the art of blood flow determination, may be used.

There is thus provided in accordance with a preferred embodiment of the invention, a vaginal probe system, comprising:

a shaft having a diameter of between 20 and 32 mm and adapted for insertion at least 5 mm into a human female genitalia; and a stimulator comprising at least one stimulation area, said stimulation area being defined on only a portion on the shaft, said stimulator being configured to stimulate only a portion of the genitalia corresponding to said stimulation area There is also provided in accordance with a preferred embodiment of the invention, a vaginal probe system, comprising:

a shaft adapted for insertion at least 5 mm into a human female genitalia; and a vibration stimulator comprising at least one stimulation area, said stimulation area being defined on only a portion on the shaft, said stimulator being configured to stimulate only a portion of the genitalia corresponding to said stimulation area.

There is also provided in accordance with a preferred embodiment of the invention, a vaginal probe system, comprising:

a shaft adapted for insertion at least 1 mm into a human female genitalia;

a stimulator comprising at least one stimulation area, said stimulation area being defined on only a portion on the shaft, said stimulator being configured to stimulate only a portion of the genitalia corresponding to said stimulation area; and means for urging said area against said portion, at a desired pressure level.

In a preferred embodiment of the invention, said stimulation comprises stimulation using heat. Alternatively or additionally, said stimulation comprises stimulation using cold. Alternatively or additionally, said stimulation comprises stimulation using vibration. Alternatively or additionally, said stimulation comprises stimulation using electrical current.

Alternatively or additionally, said stimulation area is adapted for contact with a clitoris. Preferably, the system comprises circuitry for activating said stimulation area to generate a sub-threshold stimulation level, which stimulation is below a normal sensitivity of a clitoris.

Alternatively or additionally, said stimulation area is adapted for contact with a portion of a vagina. Preferably, the system comprises circuitry for activating said stimulation area to generate a sub-threshold stimulation level, which stimulation is below a normal sensitivity of a vagina.

In a preferred embodiment of the invention, said stimulation area is adapted for contact with a portion of a lip of said genitalia.

In a preferred embodiment of the invention, said shaft is substantially cylindrical. Preferably, said shaft has a diameter of between 20 and 32 mm. Alternatively or additionally, said shaft has a diameter of between 23 and 30 mm. Alternatively or additionally, said shaft has a diameter of about 28 mm.

In a preferred embodiment of the invention, said shaft has a length of between 60 and 250 mm. Alternatively or additionally, said shaft has a length of between 80 and 130 mm. Alternatively or additionally, said shaft has a length of about 150 mm.

In a preferred embodiment of the invention, said shaft is adapted for insertion at least 20 mm into said genitalia. Alternatively or additionally, said shaft is adapted for insertion at least 40 mm into said genitalia. Alternatively or additionally, said shaft is adapted for insertion at least 60 mm into said genitalia. Alternatively or additionally, said shaft is adapted for insertion at least 100 mm into said genitalia.

In a preferred embodiment of the invention, said shaft comprises an inner probe portion and an outer hull. Preferably, said outer hull is flexible. Alternatively, wherein said outer hull is rigid.

In a preferred embodiment of the invention, the system comprises an actuator which moves said inner portion relative to said outer hull. Preferably, said actuator axially moves said inner hull. Alternatively or additionally, said actuator said actuator rotates said inner hull relative to said outer hull.

In a preferred embodiment of the invention, said outer hull is water tight.

In a preferred embodiment of the invention, the system comprises an extension which remains outside of said genitalia, when said shaft is inserted therein. Preferably, the system comprises a base coupled to said extension. Preferably, said base is weighted to stabilize said probe from moving out of position.

In a preferred embodiment of the invention, the system comprises means for attaching said extension to a patient comprising said genitalia.

In a preferred embodiment of the invention, the system comprises means for attaching said extension to a bed on which a patient comprising said genitalia is placed.

In a preferred embodiment of the invention, the system comprises an urging means for urging a portion of said stimulation area against said portion of said genitalia Preferably, said urging means comprises at least one counterweight. Alternatively or additionally, said urging means maintains a desired pressure on said stimulation area.

In a preferred embodiment of the invention, the system comprises an external controller for said system, which controls at least one parameter of the stimulation of at said stimulation area. Preferably, said at least one parameter comprises a stimulation duration. Alternatively or additionally, said at least one parameter comprises a stimulation intensity. Alternatively or additionally, said at least one parameter comprises a stimulation modality. Alternatively or additionally, said at least one parameter comprises a variation of a parameter over time. Alternatively or additionally, said at least one parameter comprises a delay between consecutive stimulations.

In a preferred embodiment of the invention, said controller includes an input for receiving a patient response to said stimulation. Preferably, said controller includes a memory for storing said input in association with stimulation parameters used to elicit said response. Alternatively or additionally, said controller modifies said at least one stimulation parameter, responsive to said input. Alternatively or additionally, said controller includes software for driving said stimulation area according to a nervous-sensitivity testing protocol. Preferably, said protocol is adapted to take into account an arousal level of said patient as a result of said stimulation.

In a preferred embodiment of the invention, said shaft is connected to said controller by wire. Preferably, said shaft is transmits data to said controller by wireless means.

In a preferred embodiment of the invention, said stimulation area is substantially square. Alternatively, said stimulation area is substantially round.

In a preferred embodiment of the invention, said stimulation area is at a side of said shaft. Alternatively, said stimulation area is at an end of said shaft. Alternatively, said stimulation area rings said shaft.

In a preferred embodiment of the invention, said stimulation area is flush with said shaft. Alternatively, said stimulation area protrudes from said shaft.

In a preferred embodiment of the invention, said stimulation area is less than 1500 mm square in area. Preferably, said stimulation area is less than 500 mm square in area Preferably, said stimulation area is less than 200 mm square in area. Preferably, said stimulation area is less than 70 mm square in area. Preferably, said stimulation area is less than 30 mm square in area. Preferably, said stimulation area is less than 10 mm square in area.

In a preferred embodiment of the invention, said at least one stimulation area comprises at least two separate stimulation areas on said shaft. Preferably, said separate areas can be independently activated to stimulate.

In a preferred embodiment of the invention, said at least one stimulation area comprises at least four separate stimulation areas on said shaft.

In a preferred embodiment of the invention, said at least one stimulation area comprises at least a ten separate stimulation areas on said shaft.

In a preferred embodiment of the invention, said shaft is sterilizable.

In a preferred embodiment of the invention, the system comprises at least one local physiological sensor on said shaft. Preferably, said sensor is a sensor which detects changes in blood flow. Alternatively or additionally, said sensor is adjacent said stimulation area.

In a preferred embodiment of the invention, said shaft includes an interior lengthwise channel from outside said body to said genitalia.

There is also provided in accordance with a preferred embodiment of the invention, a method for assessing a sensitivity of a female genitalia, comprising:

contacting a portion of said genitalia with a localized stimulator at a desired contact pressure;

activating said stimulator at least once to selectively stimulate said portion; and determining at least one threshold of nervous sensitivity of said portion based on a patient response to said stimulation. Preferably, said patient response is determined by a conscious response of said patient. Alternatively or additionally, said patient response is determined by a autonomous response of said patient. Preferably, said autonomous response is determined by measuring a change in blood flow responsive to said stimulation. Preferably, said blood flow change is determined by imaging at least a portion of said genitalia.

In a preferred embodiment of the invention, said blood flow change is determined by imaging at least a portion of a brain of said patient. Alternatively or additionally, said blood flow change is determined by a sensor in contact with the stimulated area.

In a preferred embodiment of the invention, said desired contact pressure is maintained over said at least one activation of said stimulator.

In a preferred embodiment of the invention, said desired contact pressure is intentionally varied for different parts of said genitalia.

In a preferred embodiment of the invention, the method comprises varying a delay between subsequent activations responsive to said patient response.

In a preferred embodiment of the invention, said threshold comprises a sensation threshold. Alternatively or additionally, said threshold comprises a pain threshold. Alternatively or additionally, said threshold comprises a pleasure threshold. Alternatively or additionally, said threshold comprises a comfort threshold.

In a preferred embodiment of the invention, the method comprises varying at least one parameter of said activation for different activations of the same portion. Preferably the method comprises varying a duration of said activation. Alternatively or additionally, the method comprises varying an intensity of said activation. Alternatively or additionally, the method comprises varying a stimulation modality of said activation.

In a preferred embodiment of the invention, the method comprises varying at least one parameter of said activation for activations of different portions. Preferably, said varying comprises replacing said probe with a different probe. Preferably, said probes are exchanged while maintaining a same holder in a same relative position to said genitalia.

In a preferred embodiment of the invention, the method comprises repeating said selectively stimulating and said determining for a plurality of portions of said genitalia. Preferably, the method comprises generating a threshold map of a portion of said genitalia.

In a preferred embodiment of the invention, said portion comprises a portion of a vagina Alternatively or additionally, said portion comprises at least a portion of a clitoris.

In a preferred embodiment of the invention, selectively stimulating comprises inserting a stimulator into said genitalia.

In a preferred embodiment of the invention, determining comprises selectively stimulating said portion at a plurality of stimulation levels. Preferably, said determining comprises determining using a limits method.

In a preferred embodiment of the invention, selectively stimulating comprises maintaining a background stimulation of at least another part of said genitalia. Preferably, said at least another part comprises substantially all of a vagina of said genitalia.

There is also provided in accordance with a preferred embodiment of the invention, a method for assessing a sensitivity of a female genitalia, comprising:

contacting at least portion of said genitalia with a stimulator;

activating said stimulator at least once to stimulate at least said portion; and determining at least one threshold of nervous sensitivity of said portion based on an autonomous response to said stimulation. Preferably, said stimulating is restricted to said portion. Alternatively or additionally, said determining is by imaging of said genitalia.

In a preferred embodiment of the invention, the method comprises repeating said stimulating in a pattern which models a sequence of activities in a sex act.

BRIEF DESCRIPTION OF FIGURES

The invention will be more clearly understood by reference to the following description of preferred embodiments thereof read in conjunction with the accompanying figures. Identical structures, elements or parts that appear in more than one of the figures are labeled with a same or similar numeral in all the figures in which they appear.

DETAILED DESCRIPTION OF PREFERRED EMBODIMENTS

Figure 1:
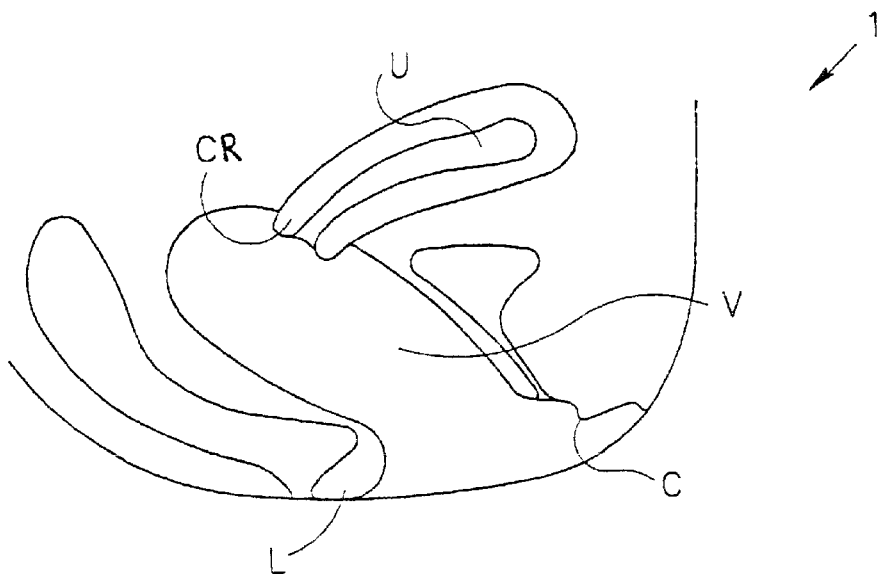
FIG. 1 is a schematic cut-through illustration of a female pelvic region, showing the internal and external sexual organs.

FIG. 1 is a schematic cut-through illustration of a female pelvic region, showing the internal and external sexual organs of a subject. Generally, the sexual organs comprise a uterus U which is capped by a cervix CR. A vagina V forms a channel between the uterus and the exterior of the body. Lips L form a mouth at the entrance to vagina V and also enclose a clitoris C. In the course of sexual intercourse, a penis (not shown) is inserted in vagina V. A significant portion of the pleasure during sexual intercourse is a direct result of stimulation of clitoris C and of vagina V, by the movement of the penis. As can be appreciated, if vagina V and/or clitoris C suffer from hyper- or hypo- sensitivity, the amount of sexual pleasure may be significantly reduced or even replaced by pain.

Figure 2:
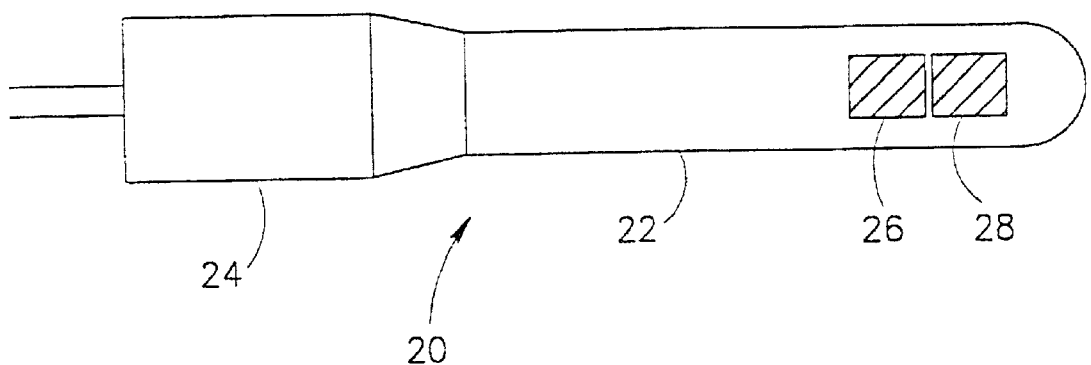
FIG. 2 is a schematic illustration of a vaginal probe, in accordance with a preferred embodiment of the invention.

FIG. 2 is a schematic illustration of a vaginal probe 20, for determining a sensitivity level of vagina V, in accordance with a preferred embodiment of the invention. Probe 20 is preferably formed of a shaft 22 for insertion in vagina V, and preferably including a stop 24 which forms a thickening in shaft 22. Probe 20 preferably includes at least one stimulation element (area) 26, which is used to provide a stimulus having known physical parameters to a part of vagina V. Preferably, a subject responds to a stimulation of her vagina by indicating a sensation caused by the stimulation. Preferably, probe 20 is connected to a computer and/or dedicated hardware and/or software (not shown) which control the stimulation and/or on which the response of the subject is stored. Typically, the subject may respond verbally and/or by pressing a switch or other control which is connected to the computer.

In a preferred embodiment of the invention, the stimulation may include one or more of:

a) Temperature. The temperature stimulus is preferably applied relative to an ambient vaginal temperature which is typically 36° C. or 37° C. Preferably, the temperature is measured using a temperature sensor on the probe. Typical sensation thresholds are about 1–2° C. from the ambient. Typical pain thresholds are about 45° C. and 5–15° C. However, the applied stimulation may cover any value in the range, especially for an abnormal physiology. Both heat and cold stimulations may be applied. Preferably, the temperature is applied at a temperature change rate is between 0.1 and 20 degrees Celsius/second. More preferably, the change rate is between 0.5 and 4 degrees/second. In a preferred embodiment of the invention, probe 20 includes a safety cut-off feature which stops the heating of active area 26 if it is outside a predetermined safety level, such as 0–50° C. Alternatively or additionally, the temperature safety limit includes also a time limit, at extreme temperatures. In a preferred embodiment of the invention, the heating/cooling is cut-off using a thermostat. Alternatively or additionally, a special software routine is provided in a computer which controls the probe, to unconditionally turn-off or reverse the heating/cooling if a predefined safety range of temperatures is exceeded. The temperature of the active areas of the probe is preferably provided using a temperature sensor on probe 20.

b) Vibration. Vibration may be axial, radial and/or rotational. Alternatively or additionally, various frequencies and amplitudes may be tested, for example frequencies in the range 0.5–400 Hz and/or amplitudes in the range 0.1 micron to 500 micron. Alternatively or additionally, various motion wave forms may be used, for example square waves, saw-tooth waves and /or sine-waves. As noted above, with respect to temperature, any intermediate value of vibration parameters may be applied as well. Also, more extreme values may be applied. Alternatively or additionally, vibration may include large scale motion, for example in the order of millimeters or even centimeters.

c) Electrical stimulation. Various stimulation waveforms, voltage, current, frequencies, periods, repetition envelopes and polarities are known in the art of electrical stimulation of nerves and may be applied as required. For example, the wave form can be square wave, bipolar impulse, sine-wave or saw-tooth. Also, non-periodic wave-forms may be applied. The voltage may be, for example, between 0.1 and 10 Volts. The current may be between 0.001 mA and 1 A. A frequency may be, for example, between DC and 6 kHz. Additionally, the area which is stimulated may also be controlled. In some cases a stimulation signal may be selected (voltage level, waveform and/or frequency) so that it does not directly affect nerves and/or muscle fibers, so that only indirect sensations are monitored.

d) Pressure. In a preferred embodiment of the invention, pressure is applied by extending a projection from active area 26. Alternatively or additionally, projections may be extended from two opposite sides of probe 20. Alternatively or additionally, the circumference of probe 20 may be increased. Applicable parameters include area and/or cross-section of the projecting area, projection speed, projection amplitude and/or projection pressure. Alternatively or additionally, pressure may be controlled by moving the probe relative to the vagina or the clitoris, for example by using counterweights, or by manual movement of the probe by an operator of the probe. In a particular implementation, a force of between 50 and 150 grams was found to be suitable.

These stimulations are preferably applied via active area 26. Alternatively or additionally, a second active area 28 may be provided adjacent area 26, or distanced therefrom, for example, for passing an electrical current between them or for simultaneously stimulating at two locations. In a preferred embodiment of the invention, an active area comprises an electricity, vibration and temperature conducting layer. Behind the active area, a piezoelectric element may be used to excite vibrations in the active area. Alternatively or additionally, an electromagnetic vibrator may be used. An electro-thermal effect heater/cooler, preferably a Peltier element, may be used to set a temperature of an active area. Preferably, probe 20 includes a thermal sink fluid, such as water, which may be circulated through the probe to absorb heat or cold generated by the side of the Peltier element which is inside the probe. Alternatively or additionally, an electric heater may be used to apply a heat stimulus. Preferably, the electric heater is a flat resistive type electric heater. In a preferred embodiment of the invention, an electrical lead may be used to provide an electric current, for electrical stimulation. Alternatively or additionally, one or more of the above stimulation functions may be provided via a second active area or using sub elements of the active area. In a preferred embodiment of the invention, insulating material (vibration, electrical and/or thermal) is preferably provided around active area 26, so that the stimulation remains local and does not spread substantially beyond area 26.

Alternatively or additionally, to the stimulations (e.g., temperature, electricity, vibration) being local they may be applied to a significant portion of vagina V. In one example, the entire shaft 22 of probe 20 may be axially vibrated at 10 Hz with an amplitude of between 0.1 micron and 200 micron.

In a preferred embodiment of the invention, area 26 is flush with the probe. Alternatively, area 26 may extend outwards from the probe. In the case of a probe for the clitoris, area 26 may be concave, for example to surround the clitoris. The desired contact area in such a concave active area may be, for example, the center of the area and/or its sides. Alternatively, a narrow tip probe, for example with a diameter of 1 mm may be used, especially for detailed mapping of the clitoris.

The protocols used may include any of those known for use in peripheral nerve evaluation, including: limits method (where a patient announces when a threshold is reached), staircase and level tests (where the stimulation increases as a staircase and responses to different levels are tested), forced choice and suprathreshold. An example of a peripheral nerve evaluation system is a TSA-2001, available from Medoc Ltd., of Ramat Yishai, Israel. A description of various test protocols is available in a user guide provided with the system, the disclosure of which is incorporated herein by reference and also described in Israel patent application number 126,723 by applicant Medoc Ltd., the disclosure of which is incorporated herein by reference.

In some preferred embodiments of the invention, the stimulations are constant. Alternatively, they (amplitude, frequency, etc.) may vary, within a single stimulation. In a preferred embodiment of the invention, the probe is tested against an outside portion of the patient, such as the skin (e.g., on the hand), for example to calibrate the probe, to test the patient responses and/or to explain the functioning of the device to the patient.

In a preferred embodiment of the invention, the computer may be used to store data, such as patient data, historical data and current results data. Alternatively or additionally, the computer may be used to store measurement programs, especially for spatial and/or non-spatial mapping, described below. Alternatively or additionally, the software may comprise a "WinTSA" program, which is provided in conjunction with the above TSA-2001 probe system and which manages testing and controlling of a TSA-2001 probe.

In a preferred embodiment of the invention, the diameter of probe 20 is selected to emulate a diameter of a penile shaft. Preferably, the diameter is between 20 mm and 32 mm. More preferably, the diameter is between 23 mm and 30 mm. In an exemplary embodiment, the diameter is about 28 mm. However, larger diameters may also be used. Preferably, the length of an insertable portion of probe 20 is between 60 mm and 250 mm. More preferably, between 80 mm and 130 mm. In an exemplary embodiment, about 150 mm. Alternatively, a narrow shaft may be used, however, it is preferably long enough to reach a desired portion of the vagina. For stimulating only the clitoris, a probe may be shorter and have a thicker diameter. However, the probe is preferably thin enough and long enough so that it does not contact other body parts besides the clitoris. The active area for a clitoris probe is preferably at the tip of the probe, preferably axial, but possibly off axis.

Active areas 26 and 28 are preferably 16×16 mm each and are preferably coated with or formed of anodized aluminum, stainless steel, platinum or other non-bio-reactive metals. However, other sizes and shapes of active areas may be used, for example, a circle, for example of 10 mm diameter. In particular, small active areas may be provided, for example between 1 m and 5 mm in extent. Probe 20 itself is preferably formed of Delarin. Alternatively or additionally, the probe may be formed of a material having desired thermal transfer behavior, such as being similar to human flesh. It should be noted that the probe is in contact with mucus tissue of the body. As such, and substantially unlike peripheral sensing probes, sterilization is an issue. In a preferred embodiment of the invention, probe 20 is sterilized by immersion in Cydex, Biocide or Lysol. Alternatively, some type of one-time probe is used, for example as described below.

Vagina V comprises soft and elastic tissue. As such, once active area 26 is moved away from a particular location on vagina V, there may be difficulty in later returning to the same location, for example, to perform a repeat measurement. In a preferred embodiment of the invention, a probe is provided which has a portion which maintains a fixed position and/or orientation relative to vagina V, while a second portion of the probe may be moved to stimulate different parts of vagina V.

Figure 3:
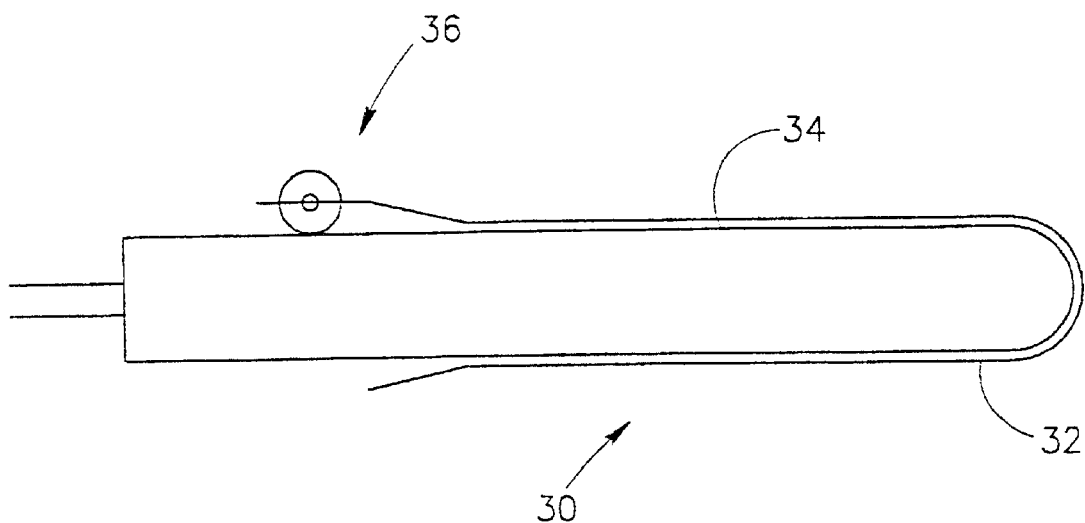
FIG. 3 is a schematic illustration of a two layer vaginal probe in accordance with a preferred embodiment of the invention.

FIG. 3 is a schematic illustration of a two layer vaginal probe 30, which provides this feature, in accordance with one preferred embodiment of the invention. Probe 30 preferably includes an outer hull 32 and an inner, movable, probe portion 34. In a preferred embodiment of the invention, probe 30 includes a relative movement device, such as a gear 36, which controls the relative displacement of hull 32 and inner probe 34. Preferably, gear 36 controls axial displacement. Alternatively or additionally, gear 36 controls angular rotation. Alternatively or additionally to a relative movement device, probe 30 may include a relative position indicator, for example using markings on hull 32 and/or inner probe 34 and/or an encoder on the shaft of gear 36. It should be appreciated that in some embodiments, all the interface of inner probe 34 with the body is through hull 32, so that inner probe 34 does not need to have any particular shape to conform to the vagina. Nor does it need to be water resistant.

In a preferred embodiment of the invention, hull 32 is manufactured as a single use outer element. Preferably, the hull forms a sterile barrier between inner probe 34 and vagina V. Alternatively at least an inner portion of hull 32 is disposable. Alternatively or additionally, hull 32 is made of a smooth and/or easily sterilized material, for example, a material suitable for microwave or ethylene sterilization. Alternatively or additionally, probe 20 may be used only for a single patient, so that no transfer of microbes will occur between patients. A perpatient probe (non necessarily single use) is also useful if the probe is mechanically deformed to match a physiology of a particular patient. In a preferred embodiment of the invention, hull 32 is flexible, for example a condom and may be coupled by friction to inner probe 34. Alternatively or additionally, hull 32 is rigid, for example screwing or clipping on to a base of probe 30.

In operation, hull 32 is inserted into vagina V and fixed in place. Inner probe 34 is then preferably inserted to a desired axial and/or rotational position, so that an active area thereon is in contact with a portion of vagina V to be tested. In some embodiments, hull 32 is deformable, so hull 32 may be inserted into vagina V using an insert or while inner probe 34 is inside of it. In a preferred embodiment of the invention, hull 32 comprises a solid material, so inner probe 32 does not have any direct contact with vagina V (but is preferably directly mechanically coupled to vagina V). Preferably, a lubricant is provided between inner probe 34 and hull 32. Alternatively, no lubricant is used. Preferably, hull 34 is thin enough to conduct heat and vibration across it, with only a small loss. Preferably, the material of hull 32 is a low quality conductor of heat and/or vibration, so that an effective active area on hull 32 is substantially a same size as on inner probe 34. In some cases, if hull 32 is thin enough, even a good conductor of heat/vibration will not have a significant lateral conduction. Alternatively or additionally, hull 32 may non-isotropic, for example comprising a lattice of conducting elements, (axially) separated by non-conducting filler. Thus, heat, vibration and/or electricity are easily conducted across the hull but not along it. Preferably, the size of conducting elements is smaller than a distance between active area 26 and active area 28, so that they do not cause a short circuit.

Alternatively, hull 32 may comprises an open mesh, whereby the mesh remains in place relative to vagina V, but it does not interpose between inner probe 34 (especially the active areas) and vagina V, so there is direct contact of most of inner prone 34 and vagina V.

In an alternative embodiment, outer hull 32 is transparent, at least at some locations thereof to infra-red radiation and heating stimulation is achieved using an infrared which is comprises in inner portion 34.

In a preferred embodiment of the invention, hull 32 has a rough and/or bumpy exterior, so that it does not move relative to vagina V. Alternatively or additionally, hull 32 may have a non-circular cross-section, for example oval or polygonal. Alternatively or additionally, probe 30 includes straps and/or other fixing elements (not shown) to anchor probe 30 relative to the body the subject. Alternatively or additionally, probe 30 (or probe 20) includes a holder which is external (mostly or completely) to the body of the patient. The holder is preferably fixed to the patient, a bed or to a support element attached to a floor, or it may include a heavy base. In an alternative embodiment, the probe is mounted on an articulated arm, to allow orienting the probe at substantially arbitrary orientations and positions relative to the patient. In a preferred embodiment of the invention, a suitable contact between the probe and a portion of vagina V is assured by mechanical means, for example, a spring in the bolder (which pushes against the probe in a desired direction) and/or by a weight which performs a similar function.

In an alternative embodiment, the probe may be a completely insertable probe which is inserted in the vagina without an external base. Possibly, a wire connects the probe to external equipment. Alternatively, the probe may be wireless, with an internal power source. Such a wireless probe is also useful in an embodiment having an external base, as it eliminates the need for wires. Alternatively or additionally, the probe may be manufactured in the form of a finger covering, for example a thimble or a one-finger glove, to allow an operator of the probe to position the probe using his/her finger.

In a preferred embodiment of the invention, a probe, especially a wireless probe is left in the vagina for a considerable period of time, for example an hour, overnight or several days. Such a probe preferably measures a patient's autonomous responses to stimulation. Alternatively or additionally, the device can measure the changes in arousal level not due to stimulation by the device. Optionally, a user input, such as a hand-held control is in wired or wireless contact with the probe to allow a patient to respond to stimulation, these responses and/or measurements are preferably stored on the probe. It should be noted that the autonomous response can include several parameters, for example including one or more, response time, decay time, amplitude and envelope.

Figure 4:
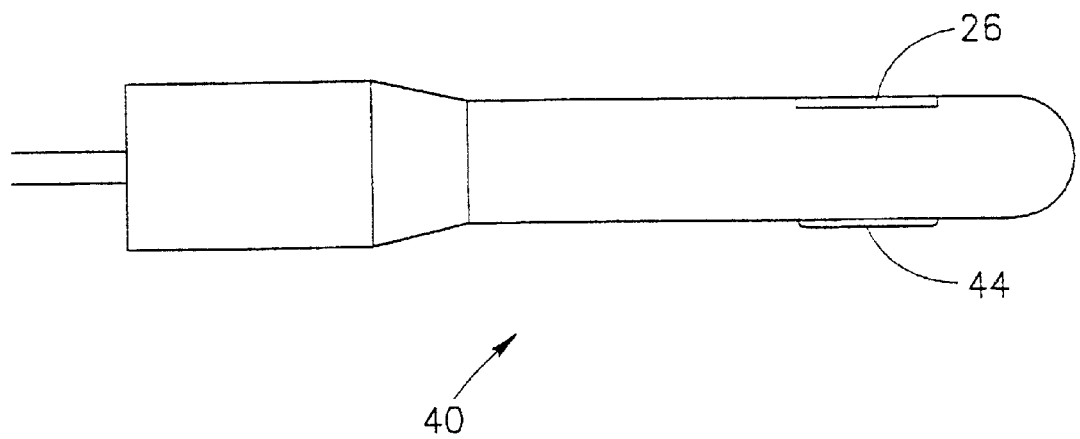
FIG. 4 is a schematic illustration of vaginal probe including a contact assuring device, in accordance with a preferred embodiment of the invention.

It is often desirable to assure that a good contact is formed between an active area 26 and a portion of vagina V. In a preferred embodiment of the invention, the probe includes an element which causes such a contact. FIG. 4 is a schematic illustration of vaginal probe 40 including a contact assuring device 44, in accordance with a preferred embodiment of the invention. Preferably, device 44 comprises an inflatable balloon located radially opposite active area 26. When the balloon is inflated, probe 40 and area 26 are pushed against the opposite wall of vagina V. Alternatively or additionally, a balloon may be provided underlying area 26, so that only area 26 is pushed against the wall of vagina V.

Alternatively or additionally, area 26 and/or a portion of probe 40 surrounding it include a suction element, for example a vacuum pump outlet, to draw the vagina surface to area 26.

Alternatively or additionally to attempting to assure a good contact, the quality of the contact between active area 26 and vagina V may be measured, for example using a pressure sensor or an impedance sensor. This measurement may be logged for analysis. Alternatively or additionally, this measurement may be used to control the contact pressure, for example, using an actuator. Alternatively or additionally, the contact pressure may be used to trigger the stimulation when a desired pressure is achieved.

In a preferred embodiment of the invention, a balloon or other controllably deformable expandable structure may also be used to provide tactile stimuli. In one example, balloon 44 includes small projections (not shown). When the balloon is inflated, these projections poke into the vagina. The quality of sensation of these projections may also be reported by a subject and used for evaluating nervous parameters.

Alternatively or additionally, an inflatable balloon may be used to measure a flexibility of vagina V, by determining a response curve between a radius (or volume) of the balloon and pressure therein.

Figure 5:
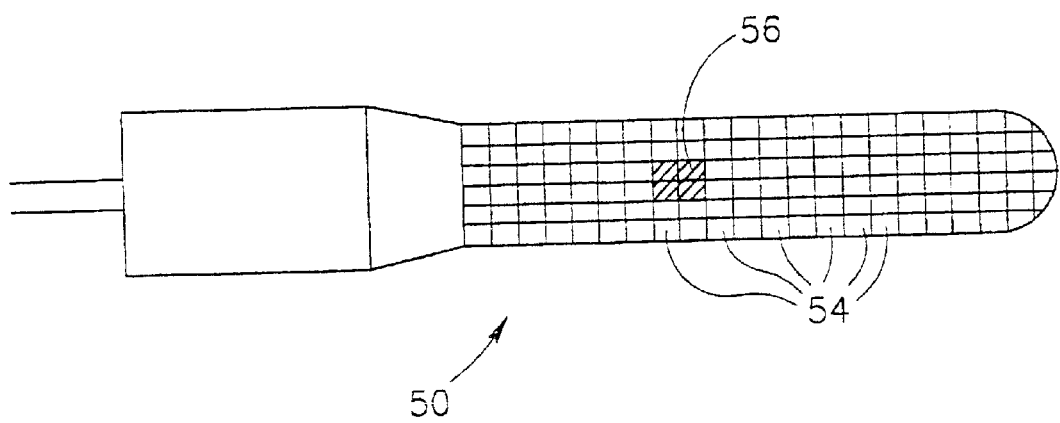
FIG. 5 is a schematic illustration of a multiple-element vaginal probe, in accordance with a preferred embodiment of the invention.

Alternatively to moving probe 20 in order to select a part of vagina V to measure/stimulate, the probe may include a selectable active area. FIG. 5 is a schematic illustration of a multiple-element vaginal probe 50, in which one or more active areas may be dynamically defined, in accordance with a preferred embodiment of the invention. In a preferred embodiment of the invention, probe 50 comprises an array having a plurality of selectively excitable sub-elements 54. In one example, an active area 56 may be defined by selecting one or more of the sub-elements to be activated, for a particular measurement. In a preferred embodiment of the invention, sub-elements 54 comprise a grid. In a preferred embodiment of the invention, various and/or arbitrary shapes of active areas 56 may be defined by suitable selection of sub-elements 54 to be activated.

In an example of vibration stimulation, the grid preferably comprises a layer of piezoelectric material with an underlying grid of electrical conductors. A similar grid of conductors may be used to provide selectable electrical excitation. In a preferred embodiment of the invention, the individually addressable elements are about 1×1 mm with a separation of 0.1 mm. However, in other embodiments of the invention, larger or smaller grid elements may be used and the spatial separation between them may be larger or smaller. It should be noted that in some embodiments only certain groupings of sub-elements are supported by the electrical circuitry which electrifies them.

Figure 6:
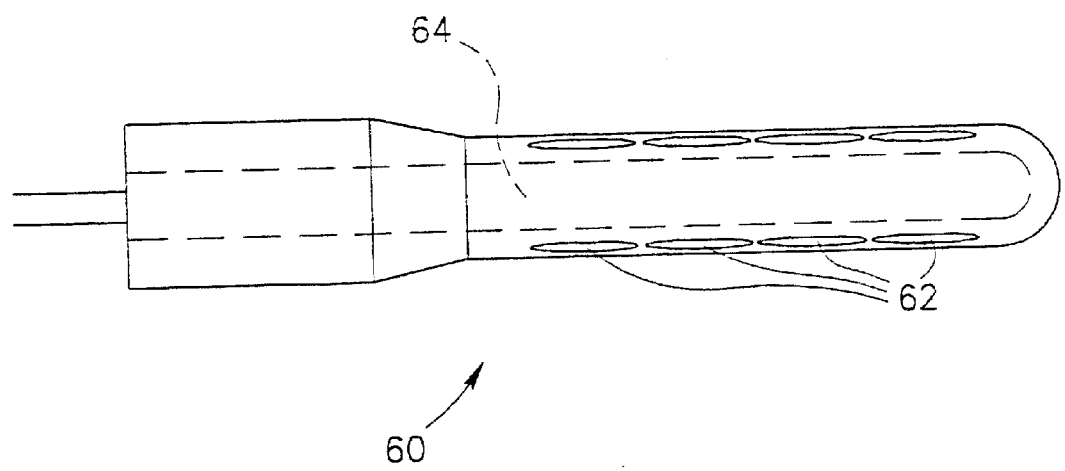
FIG. 6 is a schematic illustration of a geometrically adaptable vaginal probe, in accordance with a preferred embodiment of the invention.

It may be desirable to perform stimulation measurements in conditions which simulate sexual intercourse. In some cases, sexual dysfunction may be dependent on a shape of a penis (in which case corrective surgery of the penis or vagina may be indicated). The shape of the penis and/or its angle of penetration, may be measured using means known in the art, for example using a tape measure and/or a plaster mold. Alternatively, a plurality of different geometries may be tested on the patient, to determine certain geometries which cause pain and/or where sensation is not within desirable parameters. FIG. 6 is a schematic illustration of a geometrically adaptable vaginal probe 60, in accordance with a preferred embodiment of the invention. In a preferred embodiment of the invention, probe 60 comprises a semi-rigid material, so that probe 20 in its entirety is substantially as flexible and/or as compressible and/or distortable as a human penis. Alternatively or additionally, probe 60 may be rigid. Referring back to FIG. 3, if a hull is rigid, a softer inner probe is preferably used. Conversely, if the hull is flexible, a more rigit inner probe is preferably used.

In a preferred embodiment of the invention, the hull comprises a rigid deformable material which may by formed in the hands of a physician but which is not deformed by pressures in the vagina, during and after insertion.

In a preferred embodiment of the invention, probe 60 has a controllable diameter, so that measurements may be performed under different conditions. In such a case, a rigit hull cannot usually be used. Alternatively or additionally, a set of probes, each having a different diameter, is used. Preferably, probe 60 includes a plurality of balloons 62, which may be inflated to create a change in diameter of probe 60. Alternatively or additionally, a pressure level in balloons 62 determines a compressibility and/or a stiffness level of probe 60. Alternatively or additionally, by selective inflation of individual ones of balloons 62, probe 60 may be caused to assume a bent shape and/or deform a malleable hull.

Alternatively or additionally, probe 60 includes an inner channel 64 which can receive a shaping element (not shown). When the shaping element is inserted in channel 64, probe 60 preferably assumes a spatial shape and/or diameter dictated by the shaping element.

Thus, a probe 60 may be used to determine the effect and/or sensations caused by a plurality of probe geometrical configurations. Alternatively or additionally, an elasticity of vagina V may be determined based on a difficulty in deforming probe 60.

In a preferred embodiment of the invention, balloons 62 are inflated using pressurized fluids, preferably saline solution or air.

Unlike peripheral nerves, where each stimulation is usually independent event, a key feature of vaginal stimulation during sexual intercourse is a context in which the stimulation occurred. Thus, it is not only desired that a "base-line" vagina have a certain sensitivity threshold, but also that the vagina have a certain sensitivity characteristics during arousal. Preferably, when matching pharmaceuticals and/or other treatment and/or performing follow-up for such treatment to a particular dysfunction, it may be desirable to determine the effect to the nervous sensitivity in a variety of situations. Such a determination is also useful in drug research, when attempting to determine a myriad of effects of a pharmaceutical. Also such a determination may be useful in more accurately diagnosing a sexual dysfunction.

A particular of some embodiment of probe 60 (and/or 20, 30 40 or 50) as compared to probes used to test peripheral nerves on the body,is that probe 60 may be adapted to match a wide variety of "operating condition" in vagina V.

In peripheral nerve testing, the emphasis is typically in determining an extent of nerve damage. Sometimes nerve sensitivity is affected by local drainage, but often the testing is used to detect problems in conduction and/or central nervous system defects. In vaginal testing however, it is suspected that some at least cases of abnormal nerve sensitivity are caused by insufficient blood flow and not primary nerve damage. Additionally, in vaginal testing, it is often desirable not only to determine an extent of sexual dysfunction but also to match a treatment, which will overcome the dysfunction. Typically, what is dysfunctional in a vagina is not the nerves themselves but the tissue which includes the nerve. This tissue may be affected by drugs (for example to increase blood flow) thereby improving nervous sensitivity levels.

It should be noted that there are a large number of, possibly orthogonal, independent variables which may be controlled, including:

a) probe diameter;

b) probe geometry;

c) probe surface temperature (preferably by heating the surface of the probe using an internal electric heater (possibly also a Peltier heater/cooler);

d) base-line vibration (preferably by providing a low-level vibration over the entire surface of probe 60);

e) sexual arousal level (which may be controlled using suitable visual imagery and/or by providing direct physical stimulation using probe 60);

f) local pharmaceutical effects (which may be provided for example by topically applying a stimulating, desensitizes or vasoconstriction drug, via probe 60); and/or g) systemic drug effects (which may be provided by oral ingestion and/or injection of pharmaceuticals).

In a preferred embodiment of the invention, probe 60 includes a working channel (not shown), preferably with an opening at a side of probe 60 (e.g. active area 28) through which an actuator may be guided in to vagina V, to a known location (for example using the mechanism of FIG. 3). In a preferred embodiment of the invention, various sensors and/or stimulators may be provided through the working channel. Alternatively or additionally, pharmaceuticals may be applied using the channel. Alternatively or additionally, a visual inspection of the vagina may utilize a light guide and/or an endoscope passed through the working channel. In a preferred embodiment of the invention, a tattoo pen may be used to mark portions of the vagina at which measurements were performed and/or at which future measurements are to be taken. A visual inspection of the vagina may be used to determine a registration between the probe coordinate system and the vagina. In such a probe 60, some or all of the functional elements are provided through a working channel of probe 60, with probe 60 being substantially an endoscope through which such active elements and sensors are provided to the vagina.

In a preferred embodiment of the invention, various physiological characteristics of portions of vagina V may be measured. Preferably, these measurements are made at a same part of vagina V which is physically stimulated by probe 60. Preferably, the measurement is simultaneous with the stimulation. Alternatively or additionally, the measurement is performed after the stimulation. In a preferred embodiment of the invention, the physiological characteristics are sensed using a sensor which is passed through a working channel in probe 60. Alternatively or additionally, the sensor is integral with probe 60, preferably at an axial and/or radial offset from active area 26. Alternatively or additionally, the sensor is integral with the active area, for example, an EMG sensor may use the same electrodes as used for electrical stimulation. In another example, a pressure transducer may use the same piezoelectric transducers as a vibrator.

Other physiological parameters which may be sensed, preferably locally, mapped and/or globally, include: ultrasound and/or laser Doppler (for blood flow determination), temperature, electrical or acoustic impedance oxygenation level, blood pressure, heart rate, ECG, probe contact pressure, (autonomic) response (e.g., engorgement with blood, motion and/or increase in tension) of vagina V (or clitoris C) to electrical or other stimulation and/or various parameters of vaginal secretions, such as salinity, viscosity and amount. In some preferred embodiments of the invention, the local nature of such measurements is enhanced by providing mechanically separating the sensed area from the rest of the vagina (or clitoris). In one embodiment, this is achieved using a ring of raised material surrounding the probe. Thus, local changes in salinity may be measured, without contamination of the measurement from nearby tissue. Two or more sensed physiological parameters may be combined to form a single indication. Alternatively or additionally, the stimulation may be triggered and/or its parameters modified responsive to the measured physiological parameters.

In a preferred embodiment of the invention, the computer (or other control electronics) includes a display for the operator, for indicating if the probe is actively stimulating. Alternatively or additionally, such a display may be used to indicate a patient feedback. Alternatively or additionally, such a display may be used to indicate a measurement of one or more physiological sensors. Alternatively or additionally to the display being on the computer, the display may be on the probe, for example to allow the operator to concentrate on the probe itself. Alternatively or additionally, the probe may include a switch for controlling the probe, for example for stopping a test sequence.

Alternatively or additionally, to using a sensor on the probe to determine a patient response, functional imaging techniques, such as functional brain or body MRI, PET, SPECT and/or other imaging modalities, may be used to determine the response of the patient to the stimulation. In a preferred embodiment of the invention, the imaging is of the sex organs, for example to detect changes in temperature or to directly measure blood flow or oxygenation. Alternatively or additionally, the brain is imaged, to detect activity in the brain related to the sensing of the stimulation or to arousal caused by it. Another possibly type of imaging or measuring technique is ultrasound, which can be used to detect blood flow changes in the vaginal region, from inside r from outside the vagina. Alternatively or additionally, electrodes are used to detect changes in electrical activity and/or parameters, caused by the response. Alternatively or additionally, a temperature probe, possibly an array, on the probe may be used to detect an increase in temperature due to arousal, or a decrease due to pain. It is noted that by tracking the patient's autonomous and/or conscious responses to the stimulation, it is possible to explore the patient's response to a sequence of events, for example which model a sex act, rather than only a threshold testing as common in the art of peripheral nerve testing. Such exploring may also be useful for physiological assessment and treatment, rather than only for diagnosing physical dysfunction.

In a preferred embodiment of the invention, the image acquisition is synchronized with the stimulation, for example the stimulation driving the image acquisition using an output from the computer. Alternatively or additionally, the images may be acquired in an unsynchronized manner and suitable images are selected based on a log of when the stimulation occurred. Alternatively or additionally, the stimulator and imager may be controlled by a single clock or even the stimulator controlled by the imager.

In a preferred embodiment of the invention, nerve conduction tests are performed using the probe. In one example, a conduction of a nerve stimuli from the vagina (or a portion thereof) to a location on the spinal cord (or vice versa) is measured. The nerve conduction may be individually determined for different parts of the vagina (e.g. mapping or checking problematic areas) or alternatively or additionally to the vagina as a whole.

In a preferred embodiment of the invention, the measurement of physiological parameters are used to guide a physician in selecting which parts of a vagina to test for nerve sensitivity. In one example, nerve stimulations are applied to portions of the vagina with low blood flow. Alternatively or additionally, the physiological measurements may be guided by the stimulation measurements, for example blood flow being measured at a location with an abnormally low threshold of pain.

Alternatively or additionally, probe 60 may include an imaging sensor, such as an ultrasound sensor, to image tissues underlying a vaginal wall.

In a preferred embodiment of the invention, different parts of the vagina (and/or clitoris) or even the same part, over time, are tested using different stimulation characteristics, and/or different protocol settings. In one example, different thresholds are expected for different portions, possibly prompting different starting stimulation levels. Examples of characteristics which can be changed include probe diameter, type of stimulation, duration and other parameters described herein. In some cases, a multi-function probe may be available. In others, the probe may have to be replaced. In a preferred embodiment of the invention, only an inner portion of the probe is replaced, while an outer hull (described below) remains in place. This outer hull is preferably fixed to a base (described below) so the patient may not sense that the probe is removed. Alternatively or additionally, when a probe is replaced, some parameters of the probe are maintained, for example the probe temperature. This temperature may be set using a heater in the probe or by storing unused probes (during a procedure) in a holder which heats them to a desired temperature.

In a preferred embodiment of the invention, the response of the genitalia are tracked over time. In one example, the tracking is over a short time, such as during a session or to assess the effectiveness of a treatment. In another example, the tracking is over a long period, for example utilizing periodic checkups over several weeks, to assess the effectiveness of a treatment, such as a pharmaceutical and/or psychological treatment.

In a preferred embodiment of the invention, alternatively or additionally to measuring physiological parameters of the vagina and/or stimulation of the vagina, the measurements and/or stimulation are performed on other parts of the female sex organs, for example lips L or clitoris C.

In a preferred embodiment of the invention, a probe (10, 20, 30, 40, 50 or 60) may be used to map the stimulation and/or physiological parameters of vagina V. A grid-type probe 50 is especially useful, since it can preferably perform the mapping without being moved. Alternatively or additionally, a two-layer probe 30 may be used in which displacement of hull 32 and inner probe 34 is controlled by a computer. Preferably, the mapping is controlled by a computer. Alternatively or additionally, the control may be manual. When mapping, various resolution parameters may be defined, including, position resolution (of a center of an active area), size resolution (differentiation between active areas of different sizes), separation resolution (to see if two active areas, possibly near to each other, can be differentiated, if they are simultaneously activated and/or if they are sequentially activated). In a preferred embodiment of the invention, a result of the mapping is a map relating spatial locations with one or more locally physiological parameters and/or spatial locations. Alternatively or additionally, each map may be associated with global parameters (such as probe baseline temperature) and/or with testing conditions, such as arousal level. Thus, in some cases a three(or higher) dimensional map may be determined, for example relating spatial location, arousal level and pain threshold, for a plurality of pharmaceutical blood levels.

In a preferred embodiment of the invention, the probe includes multiple active areas, which may be activated simultaneously and/or in series, without requiring a repositioning of the probe. Alternatively or additionally, the probe may include multiple physiological sensors on its surface. Thus, in a preferred embodiment of the invention, a mapping of physiological parameters and/or stimulation may proceed at a high rate.

Figure 7:
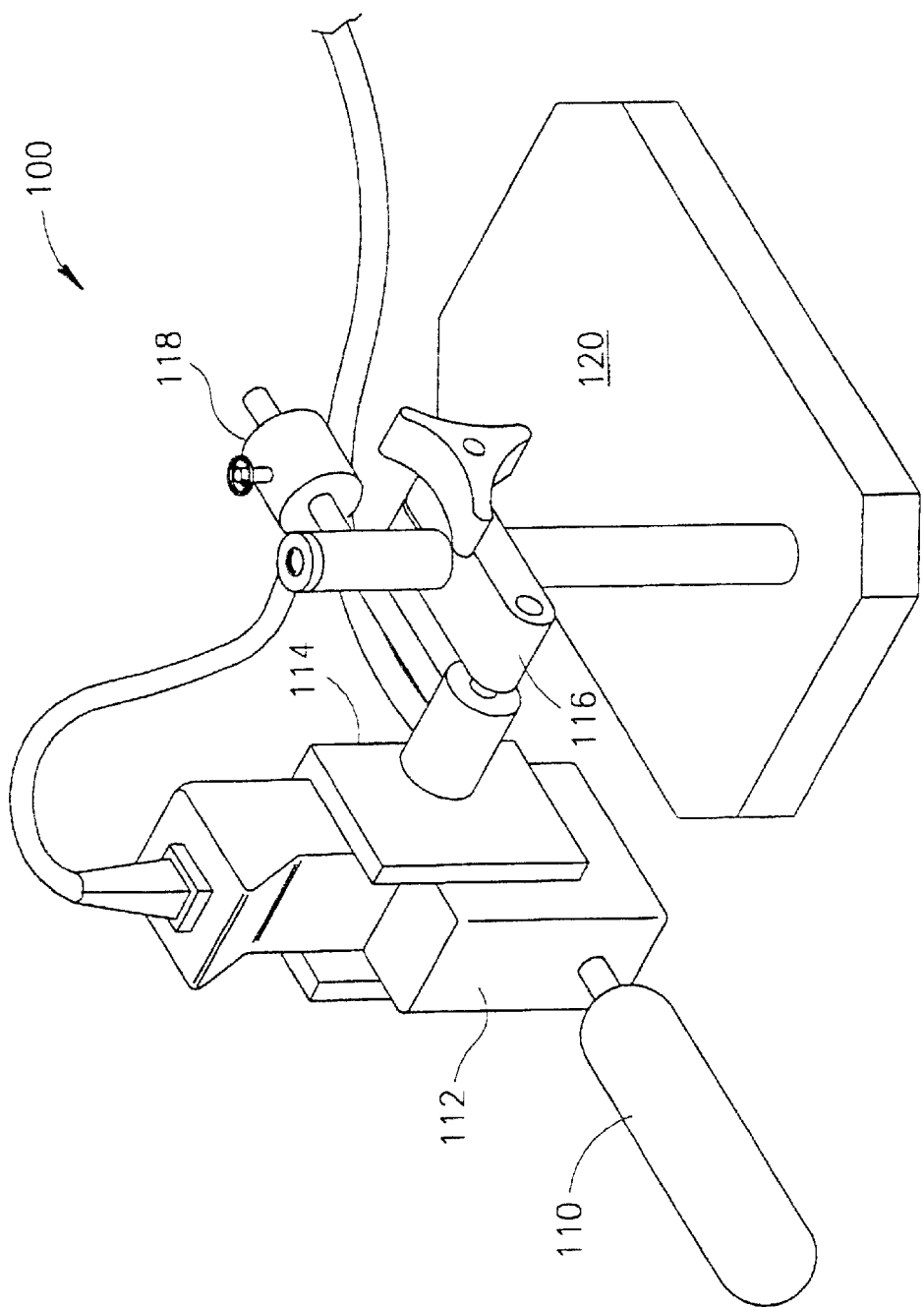
FIG. 7 is a schematic illustration of a vaginal vibration probe in a holder, in accordance with a preferred embodiment of the invention.

FIG. 7 is a schematic illustration of a vaginal vibration probe 110 in a holder 100, in accordance with a preferred embodiment of the invention. Probe 110 preferably includes an extension 112, which may house circuitry. A grasper 114 couples the probe to a base 120, through a hinge 116. A counter-weight 118 is preferably provided to balance probe 110 and/or to provide a desired contact pressure between the probe and the vagina.

Figure 8:
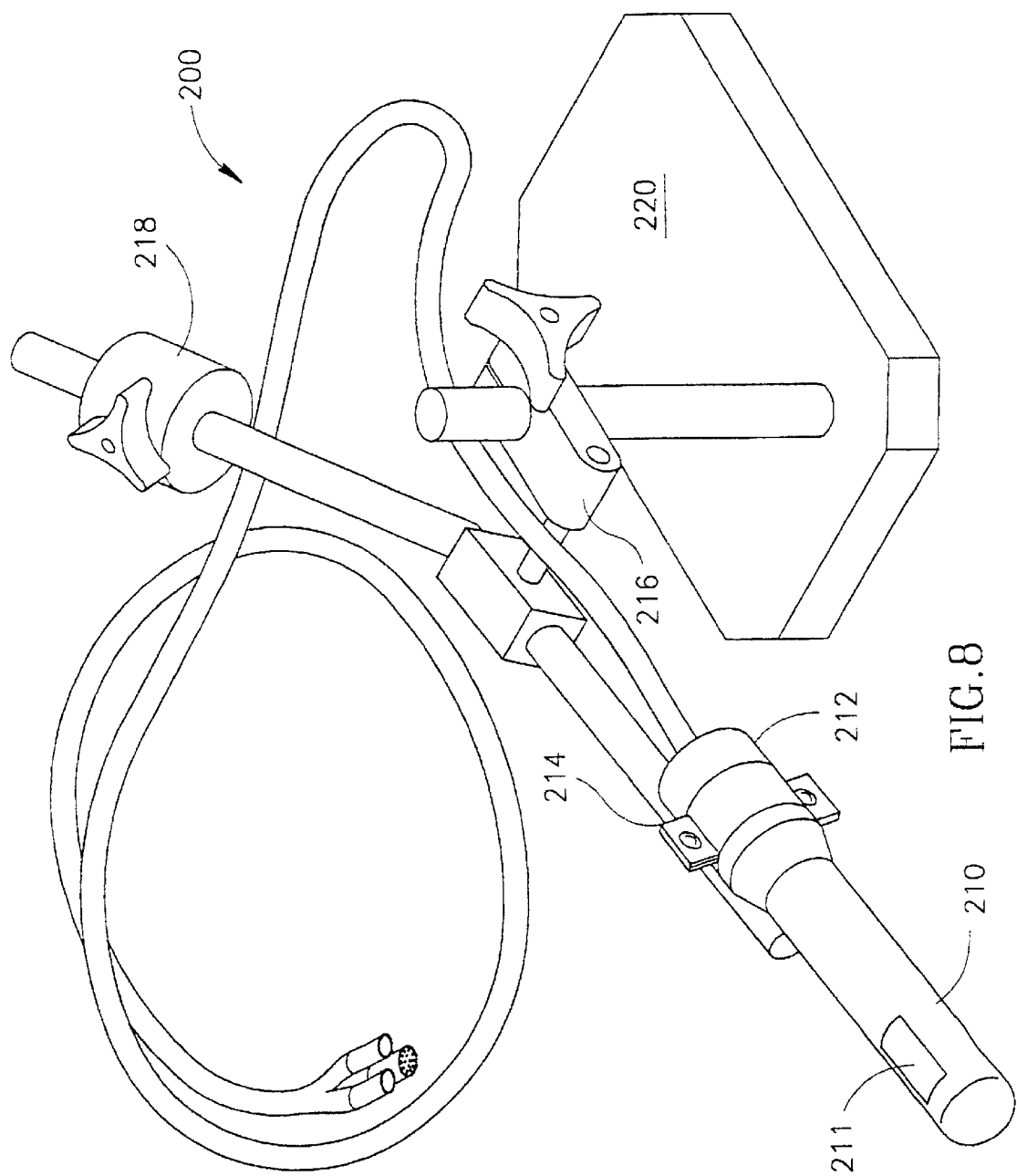
FIG. 8 is a schematic illustration of a vaginal thermal probe in a holder, in accordance with a preferred embodiment of the invention.

FIG. 8 is a schematic illustration of a vaginal thermal probe 210 in a holder 200 (possibly the same as holder 100), in accordance with a preferred embodiment of the invention. Probe 210 preferably includes an extension 212, which may house circuitry. An elongate spindle 214 couples the probe to a base 220, through a hinge 216. A counter-weight 218 is preferably provided to balance probe 210 and/or to provide a desired contact pressure between the probe and the vagina.

Figure 9:
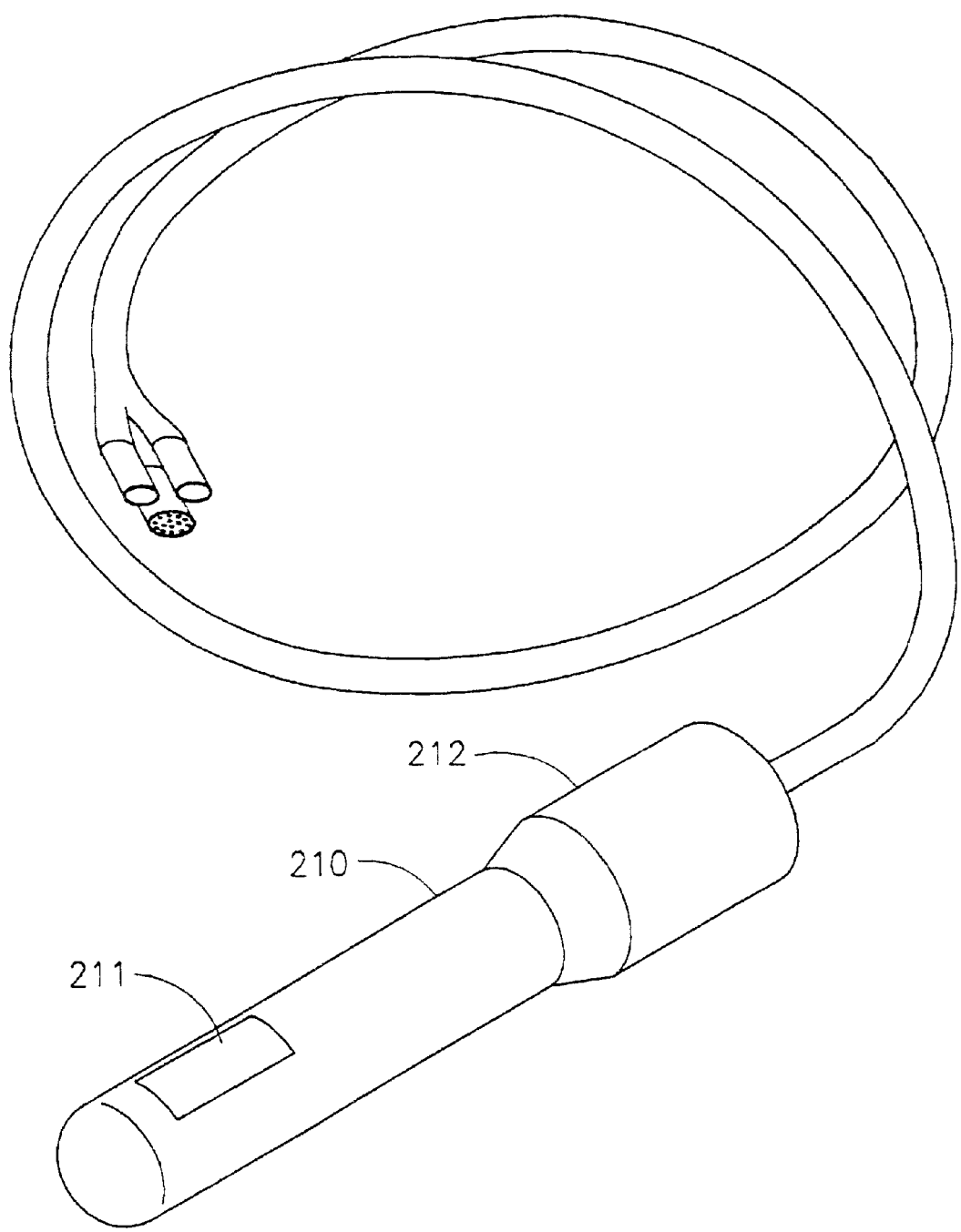
FIG. 9 is a schematic illustration of the vaginal thermal probe of FIG. 8.

FIG. 9 is a schematic illustration of the vaginal thermal probe of FIG. 8, showing in detail a rectangular active area 211, which, in an exemplary embodiment, is 16 mm by 32 mm.

Figure 10:
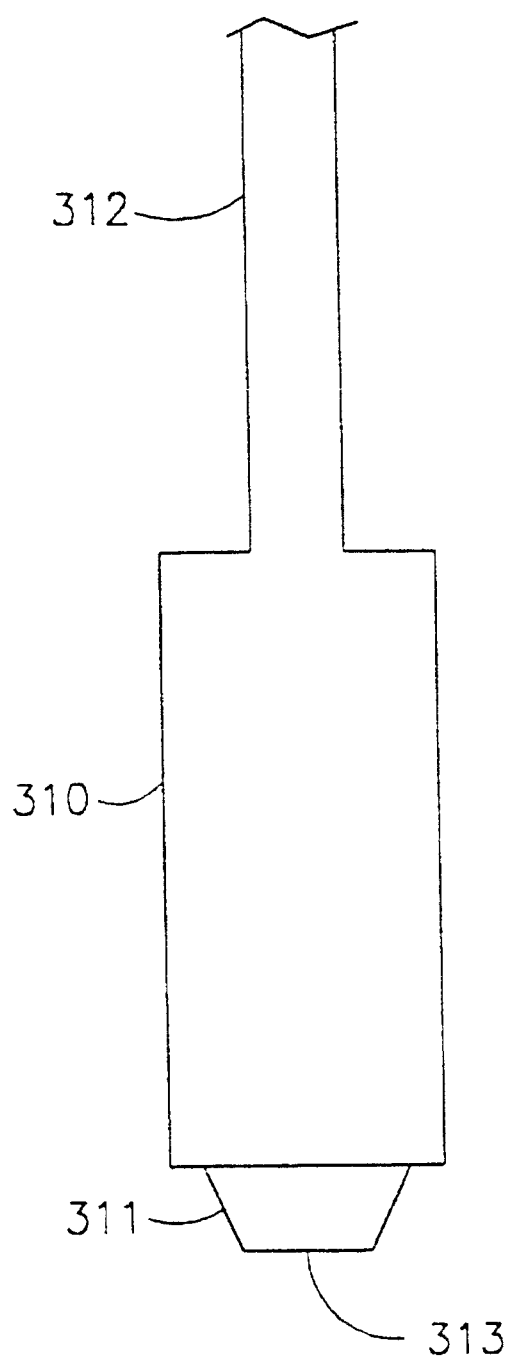
FIG. 10 is a schematic illustration of a probe for the clitoris, in accordance with a referred embodiment of the invention.

FIG. 10 is a schematic illustration of a probe 310 for the clitoris, preferably adapted for a holder such as holder 100 or holder 200, in accordance with a preferred embodiment of the invention. In a preferred embodiment of the invention, the stimulation area is at a tip 313 of the probe and/or at the sides of the tip 311. In an exemplary thermal probe, the tip area is about 25 square mm, however a smaller area may be suitable for some mapping uses. The probe length (310, not including a cable 312) is, in this exemplary embodiment, between 30 and 60 mm. Alternatively or additionally, the stimulation area is at a side of the probe, for example to allow a portion of the probe to be inserted into the vagina while stimulating the clitoris. Alternatively or additionally, two probes may be used (with one or both simultaneously active), one for the vagina and one for the clitoris. One or both of these probes may be hand-held, or they may both be attached to a holder.

In an exemplary thermal probe procedure, the probe is at a base-line temperature of between 36 and 39 degrees Celsius. The probe may be heated to such temperatures also for vibration testing. In any case, this base line temperature may be modified over the course of a single procedure, for example to determine its effect.

The higher base line temperature is one peculiarity of some vaginal probe applications as compared to "standard" peripheral nerve testing (where the baseline temperature is typically 32 degrees Celsius).

In addition, vaginal testing allows (but does not require) the introduction of the interactions between stimulations. In a simplest example, the stimulation in the vagina and clitoris has not only an effect on nerve sensory thresholds due to repeated stimulations, but also an effect caused by the response if the vaginal tissue and/or an effect caused by psychology of arousal of the patient. One result is that novel testing procedures are available. In one example, the arousal effect of a stimulation and/or interaction between consecutive stimulations, can be determined. A converse result is that to avoid interaction between stimulations, it may be necessary to monitor the psychological and/or physiological arousal of the patient, to assure that there is no undesirable interaction.

Thus, it is expected that in at least some cases, the testing procedure is modified from a standard procedure such as limits. In one example, rest period s are added when an arousal above a certain threshold is noted. In another example, certain stimulation parameters may be preferred as these lead to lesser or greater long term effects, such as interaction with adjacent stimulations. Additionally to temporal considerations, it is noted that there are also expected to be spatial interactions between stimulations in different parts of the vagina and clitoris, which interactions may be much larger than in other organs, for example a finger.

In the above description the probe has been described mainly as being useful for studies of the vagina, especially for sexual dysfunction studies. It should be noted that such testing may also yield results which are of interest for studying the pelvic base and/or the bladder, especially for rectal and/or urinary incontinence. Alternatively or additionally, a similar probe, with suitable geometrical adaptations, may also be used to perform nerve studies of the rectum.

It will be appreciated that the above described methods and apparatus of vaginal probing may be varied in many ways, for example, changing the order of steps. In addition various distributed and/or centralized configurations may be used to implement the above invention, preferably utilizing a variety of software tools. In addition, a multiplicity of various features, both of methods and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. Also within the scope of the invention are computer readable media on which software, for performing part or all of a preferred embodiment of the invention, are written. It should also be appreciated that many of the embodiments are described only as methods or only as apparatus. The scope of the invention also covers hardware and/or software adapted and/or designed and/or programmed to carry out the method type embodiments. In addition, the scope of the invention includes methods of using, constructing, calibrating and/or maintaining the apparatus described herein. As used in the following claims, the words "comprises", "comprising," "includes", "including" or their conjugates shall mean "including but not necessarily limited to".

What is claimed is:

1. A vaginal probe system, comprising:
   a shaft having a diameter of between 20 and 32 mm and adapted for insertion at least 5 mm into a human female genitalia; and
   a stimulator comprising at least one stimulation area, said stimulation area being defined on only a portion on the shaft, said stimulator being configured to selectively stimulate nerves in only a portion of the genitalia corresponding to said stimulation area, so that the stimulation remains local and does not spread substantially beyond the stimulation area.

2. A vaginal probe system, comprising:
   a shaft adapted for insertion at least 5 mm into a human female genitalia;
   a vibration stimulator comprising at least one stimulation area;
   a user input for receiving feedback on said vibration from said female; and
   a controller adapted to control said vibration in accordance with an interactive nervous testing protocol that uses user input from said input.

3. A vaginal probe system, comprising:
   a shaft adapted for insertion at least 1 mm into a human female genitalia;
   a stimulator comprising at least one stimulation area, said stimulation area being defined on only a portion on the shaft, said stimulator being configured to selectively stimulate nerves in only a portion of the genitalia corresponding to said stimulation area, so that the stimulation remains local and does not spread substantially beyond the stimulation area; and
   a pressure control mechanism operative to urge said area against said portion, at a desired controlled pressure level.

4. A system according to claim 1, wherein said stimulation comprises stimulation using heat.

5. A system according to claim 1, wherein said stimulation comprises stimulation using cold.

6. A system according to claim 1, wherein said stimulation comprises stimulation using vibration.

7. A system according to claim 1, wherein said stimulation comprises stimulation using electrical current.

8. A system according to claim 1, wherein said stimulation area is adapted for contact with a clitoris.

9. A system according to claim 8, and comprising circuitry for activating said stimulation area to generate a sub-threshold stimulation level, which stimulation is below a normal sensitivity of a clitoris.

10. A system according to claim 1, wherein said stimulation area is adapted for contact with a portion of a vagina.

11. A system according to claim 10, and comprising circuitry for activating said stimulation area to generate a sub-threshold stimulation level, which stimulation is below a normal sensitivity of a vagina.

12. A system according to claim 1, wherein said stimulation area is adapted for contact with a portion of a lip of said genitalia.

13. A system according to claim 1, wherein said shaft is substantially cylindrical.

14. A system according to claim 2, wherein said shaft has a diameter of between 20 and 32 mm.

15. A system according to claim 1, wherein said shaft has a diameter of between 23 and 30 mm.

16. A system according to claim 1, wherein said shaft has a diameter of about 28 mm.

17. A system according to claim 1, wherein said shaft has a length of between 60 and 250 mm.

18. A system according to claim 1, wherein said shaft has a length of between 80 and 130 mm.

19. A system according to claim 1, wherein said shaft has a length of about 150 mm.

20. A system according to claim 1, wherein said shaft is adapted for insertion at least 20 mm into said genitalia.

21. A system according to claim 1, wherein said shaft is adapted for insertion at least 40 mm into said genitalia.

22. A system according to claim 1, wherein said shaft is adapted for insertion at least 60 mm into said genitalia.

23. A system according to claim 1, wherein said shaft is adapted for insertion at least 100 mm into said genitalia.

24. A system according to claim 1, wherein said shaft comprises an inner probe portion and an outer hull.

25. A system according to claim 24, wherein said outer hull is flexible.

26. A system according to claim 24, wherein said outer hull is rigid.

27. A system according to claim 24, and comprising an actuator which moves said inner portion relative to said outer hull.

28. A system according to claim 27, wherein said actuator axially moves said inner hull.

29. A system according to claim 27, wherein said actuator rotates said inner hull.

30. A system according to claim 24, wherein said outer hull is water tight.

31. A system according to claim 1, and comprising an extension which remains outside of said genitalia, when said shaft is inserted therein.

32. A system according to claim 31, comprising a base coupled to said extension.

33. A system according to claim 32, wherein said base is weighted to stabilize said probe moving out of position.

34. A system according to claim 1, comprising means for attaching said extension to a patient comprising said genitalia.

35. A system according to claim 1, comprising means for attaching said extension to a bed on which a patient comprising said genitalia is placed.

36. A system according to claim 1, comprising a pressure control mechanism operative to urge at least a portion of said stimulation area against said portion of said genitalia.

37. A system according to claim 36, wherein said pressure control mechanism comprises at least one counterweight.

38. A system according to claim 36, wherein said pressure control mechanism maintains a desired pressure on said stimulation area.

39. A system according to claim 1, comprising an external controller for said system, which controls at least one parameter of the stimulation of at said stimulation area.

40. A system according to claim 39, wherein said at least one parameter comprises a stimulation duration.

41. A system according to claim 39, wherein said at least one parameter comprises a stimulation duration.

42. A system according to claim 39, wherein said at least one parameter comprises a stimulation modality.

43. A system according to claim 39, wherein said at least one parameter comprises a variation of a parameter over time.

44. A system according to claim 39, wherein said at least one parameter comprises a delay between consecutive stimulations.

45. A system according to claim 39, wherein said controller includes an input for receiving a patient response to said stimulation.

46. A system according to claim 45, wherein said controller includes a memory for storing said input in association with stimulation parameters used to elicit said response.

47. A system according to claim 45, wherein said controller modifies said at least one stimulation parameter, responsive to said input.

48. A system according to claim 45, wherein said controller includes software for driving said stimulation area according to a nervous-sensitivity testing protocol.

49. A system according to claim 49, wherein said protocol is adapted to take into account an arousal level of said patient as a result of said stimulation.

50. A system according to claim 48, wherein said shaft is connected to said controller by wire.

51. A system according to claim 39, wherein said shaft transmits data to said controller by wireless means.

52. A system according to claim 1, wherein said stimulation area is substantially square.

53. A system according to claim 1, wherein said stimulation area is substantially round.

54. A system according to claim 1, wherein said stimulation area is at a side of said shaft.

55. A system according to claim 1, wherein said stimulation area is at an end of said shaft.

56. A system according to claim 1, wherein said stimulation area rings said shaft.

57. A system according to claim 1, wherein said stimulation area is flush with said shaft.

58. A system according to claim 1, wherein said stimulation area protrudes from said shaft.

59. A system according to claim 1, wherein said stimulation area is less than 500 mm square in area.

60. A system according to claim 1, wherein said stimulation area is less than 200 mm square in area.

61. A system according to claim 1, wherein said stimulation area is less than 70 mm square in area.

62. A system according to claim 1, wherein said stimulation area is less than 30 mm square in area.

63. A system according to claim 1, wherein said stimulation area is less than 10 mm square in area.

64. A system according to claim 1, wherein said at least one stimulation area comprises at least two separate stimulation areas on said shaft.

65. A system according to claim 1, wherein said separate areas can be independently activated to stimulate.

66. A system according to claim 1, wherein said at least one stimulation area comprises at least four separate stimulation areas on said shaft.

67. A system according to claim 1, wherein said at least one stimulation area comprises at least a ten separate stimulation areas on said shaft.

68. A system according to claim 1, wherein said shaft is sterilizable.

69. A system according to claim 1, comprising at least one local physiological sensor on said shaft.

70. A system according to claim 69, wherein said sensor is a sensor which detects changes in blood flow.

71. A system according to claim 69, wherein said sensor is adjacent said stimulation area.

72. A system according to claim 1, wherein said shaft includes an interior lengthwise channel from outside said body to said genitalia.

73. A method for assessing a sensitivity of a female genitalia, comprising:
    contacting a portion of said genitalia with a localized stimulator at a desired contact pressure;
    activating said stimulator at least once to selectively stimulate said portion; and
    determining at least one threshold of nervous sensitivity of said portion based on a patient response to said stimulation.

74. A method according to claim 73, wherein said patient response is determined by a conscious response of said patient.

75. A method according to claim 73, wherein said patient response is determined by an autonomous response of said patient.

76. A method according to claim 74, wherein said autonomous response is determined by measuring a change in blood flow responsive to said stimulation.

77. A method according to claim 76, wherein said blood flow change is determined by imaging at least a portion of said genitalia.

78. A method according to claim 76, wherein said blood flow change is determined by imaging at least a portion of a brain of said patient.

79. A method according to claim 76, wherein said blood flow change is determined by a sensor in contact with the stimulated area.

80. A method according to claim 73, wherein said desired contact pressure is maintained over said at least one activation of said stimulator.

81. A method according to claim 73, wherein said desired contact pressure is intentionally varied for different parts of said genitalia.

82. A method according to claim 73, comprising varying a delay between subsequent activations responsive to said patient response.

83. A method according to claim 73, wherein said threshold comprises a sensation threshold.

84. A method according to claim 73, wherein said threshold comprises a pain threshold.

85. A method according to claim 73, wherein said threshold comprises a pleasure threshold.

86. A method according to claim 73, wherein said threshold comprises a comfort threshold.

87. A method according to claim 73, comprising varying at least one parameter of said activation for different activations of the same portion.

88. A method according to claim 87, comprising varying a duration of said activation.

89. A method according to claim 87, comprising varying an intensity of said activation.

90. A method according to claim 87, comprising varying a stimulation modality of said activation.

91. A method according to claim 73, comprising varying at least one parameter of said activation for activations of different portions.

92. A method according to claim 91, wherein said varying comprises replacing said probe with a different probe.

93. A method according to claim 92, wherein said probes are exchanged while maintaining a same holder in a same relative position to said genitalia.

94. A method according to claim 73, comprising repeating said selectively stimulating and said determining for a plurality of portions of said genitalia.

95. A method according to claim 94, comprising generating a threshold map of a portion of said genitalia.

96. A method according to claim 73, wherein said portion comprises a portion of a vagina.

97. A method according to claim 73, wherein said portion comprises at least a portion of a clitoris.

98. A method according to claim 73, wherein selectively stimulating comprises inserting a stimulator into said genitalia.

99. A method according to claim 73, wherein determining comprises selectively stimulating said portion at a plurality of stimulation levels.

100. A method according to claim 94, wherein said determining comprises determining using a limits method.

101. A method according to claim 73, wherein selectively stimulating comprises maintaining a background stimulation of at least another part of said genitalia.

102. A method according to claim 101, wherein said at least another part comprises substantially all of a vagina of said genitalia.

103. A method for assessing a sensitivity of a female genitalia, comprising:

contacting at least portion of said genitalia with a stimulator;

activating said stimulator at least once to stimulate at least said portion; and determining at least one threshold of nervous sensitivity of said portion based on an autonomous response to said stimulation.

104. A method according to claim 103, wherein said stimulating is restricted to said portion.

105. A method according to claim 103, wherein said determining is by imaging of said genitalia.

106. A method according to claim 103, comprising repeating said stimulating in a pattern which models a sequence of activities in a sex act.

107. A probe system according to claim 1, comprising a one-time sterile cover adapted to fit over said shaft and said stimulation area.

108. A system according to claim 1, wherein said shaft has a length of more than 160 mm.

109. A system according to claim 31, wherein said extension is rigid.

110. A method according to claim 73, wherein said stimulation does not affect muscle tissue adjacent said stimulation area.

111. A system according to claim 6, wherein said vibration has an amplitude of less than 500 microns.

112. A vaginal probe system, comprising:

a shaft having a diameter of between 20 and 32 mm and adapted for insertion at least 5 mm into a human female genitalia; and a stimulator comprising at least two electrical stimulation areas, said stimulation areas being defined on only a portion on the shaft, limited in both axial and circumferential extent, said stimulator being configured to selectively stimulate nerves in only a portion of the genitalia defined by said two stimulation areas to be limited in both axial and circumferential extent.

113. A probe system according to claim 112, wherein said stimulator is configured so that said stimulation does not affect muscle tissue adjacent said stimulation area.

114. A probe system according to claim 1, wherein said at least one stimulation area is limited in both axial and circumferential extent, and wherein said stimulator is configured to selectively stimulate nerves in only a portion of the genitalia defined by said at least one stimulation area to be limited in both axial and circumferential extent.

115. A probe system according to claim 1, wherein said at least one stimulation area comprises two or one stimulation areas.

116. A probe system according to claim 3, wherein said mechanism comprises a base on which said shaft is mounted and relative to which said shaft moves.

\* \* \* \* \*